US009546938B2

(12) United States Patent
Kim et al.

(10) Patent No.: US 9,546,938 B2
(45) Date of Patent: *Jan. 17, 2017

(54) COMPOSITIONS, KITS, AND METHODS FOR ISOLATING VESICLES

(71) Applicant: Samsung Electronics Co., Ltd., Suwon-si, Gyeonggi-do (KR)

(72) Inventors: Ga-hee Kim, Yongin-si (KR); Chang-eun Yoo, Seoul (KR); Ye-ryoung Yong, Seoul (KR); Myo-yong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 415 days.

This patent is subject to a terminal disclaimer.

(21) Appl. No.: 13/857,087

(22) Filed: Apr. 4, 2013

(65) Prior Publication Data

US 2014/0093880 A1   Apr. 3, 2014

(30) Foreign Application Priority Data

Sep. 28, 2012 (KR) ........................ 10-2012-0109265

(51) Int. Cl.
*C12Q 1/68* (2006.01)
*G01N 1/40* (2006.01)
*G01N 33/574* (2006.01)
*G01N 33/50* (2006.01)

(52) U.S. Cl.
CPC ............. *G01N 1/405* (2013.01); *C12Q 1/6886* (2013.01); *G01N 33/5076* (2013.01); *G01N 33/57492* (2013.01)

(58) Field of Classification Search
CPC ...................................................... G01N 1/405
USPC ........................................................ 435/6.1
See application file for complete search history.

(56) References Cited

U.S. PATENT DOCUMENTS

| | | | |
|---|---|---|---|
| 4,066,592 A * | 1/1978 | Wismer et al. | ............... 525/379 |
| 4,215,993 A | 8/1980 | Sanders | |
| 5,898,185 A | 4/1999 | Bojarczuk, Jr. et al. | |
| 6,706,551 B2 | 3/2004 | Andriessen | |
| 7,282,475 B2 | 10/2007 | Porter et al. | |
| 7,897,376 B2 | 3/2011 | Porter et al. | |
| 2004/0171077 A1 | 9/2004 | Lubenow et al. | |
| 2006/0183863 A1 | 8/2006 | Huang et al. | |
| 2009/0304677 A1 | 12/2009 | Ichim et al. | |
| 2010/0021910 A1 | 1/2010 | Cao et al. | |
| 2010/0121046 A1 | 5/2010 | Ahlquist et al. | |
| 2010/0184210 A1 | 7/2010 | Rossmanith et al. | |
| 2010/0317132 A1 | 12/2010 | Rogers et al. | |
| 2011/0018011 A1 | 1/2011 | Beeson et al. | |
| 2011/0097277 A1 * | 4/2011 | Jiang et al. | ................ 424/9.322 |
| 2011/0104052 A1 * | 5/2011 | Barnett et al. | ................ 424/1.21 |
| 2013/0256583 A1 * | 10/2013 | Schlenoff et al. | ......... 252/62.57 |

FOREIGN PATENT DOCUMENTS

| | | |
|---|---|---|
| EP | 2 544 002 A1 | 1/2013 |
| KR | 1998-070127 A | 10/1998 |
| KR | 1020120065273 A | 6/2012 |

OTHER PUBLICATIONS

Webster's New World College Dictionary, (2009) 2 cover sheets plus pp. 927 and 1669.*
Extended European Search Report for EP 13170398.5, mailed Dec. 13, 2013.
Zhang L. et al. "Imaging and cell targeting characteristics of magnetic nanoparticles modified by a functionalizable zweitterionic polymer with adhesive 3, 4-dihydroxyphenyl-L-alaine linkages", *Biomaterials, Elsevier Science Publishers BV.*, pp. 6582-6588 (2010).
Muro E. et al, "Small and Stable Sulfobetaine Zwitterionic Quantum Dots for Functional Live-Cell Imaging", *Journal of the American Chemical Society*, vol. 132, No. 13, pp. 4556-4557 (2010).
Yang W. et al., "Functionalizable and ultra stable nanoparticles coated with zwitterionic poly(carboxybetaine) in undiluted blood serum", *Biomaterials, Elsevier Science Publishers BV.*, vol. 30, No. 29, pp. 5617-5621 (2009).
Vaisocherova H. et al, "Functionalizable surface platform with reduced nonspecific protein adsorption from full blood plasma—Material selection and protein immobilization optimization", *Biosensors and Bioelectronics, Elsevier BV.*, vol. 24, No. 7, pp. 1924-1930 (2009).
Cheng G. et al., Zwitterionic carboxybetaine polymer surfaces and their resistance to long-term biofilm formation, *Biomaterials, Elsevier BV.*, vol. 30, pp. 5234-5240 (2009).
G-Biosciences Internet Catalog printout, c. 2014, (downloaded from <<http://www.gbiosciences.com/ResearchProducts/Protein-Research/Detergents-and-Accessories/Zwitterionic-Detergents.aspx>> on Mar. 18, 2015).
Sigma-Aldrich Internet Catalog printout, c. 2015 (available online at <<http://www.sigmaaldrich.com/catalog/>>; downloaded on Mar. 18, 2015).

* cited by examiner

*Primary Examiner* — Jezia Riley
(74) *Attorney, Agent, or Firm* — Leydig, Voit & Mayer, Ltd.

(57) ABSTRACT

A composition, a kit, and a method of isolating a vesicle from a sample using a compound comprising zwitterion moieties, which may be used to analyze vesicles, and proteins, glycoprotein, lipids, or nucleic acids thereof.

17 Claims, 5 Drawing Sheets

COMPOSITIONS, KITS, AND METHODS FOR ISOLATING VESICLES

CROSS-REFERENCE TO RELATED APPLICATION

This application claims the benefit of Korean Patent Application No. 10-2012-0109265, filed on Sep. 28, 2012 in the Korean Intellectual Property Office, the disclosure of which is incorporated herein by reference.

BACKGROUND

1. Field

The present disclosure relates to compositions, kits, and methods for isolating vesicles.

2. Description of the Related Art

Microvesicles are small membranous vesicles that exist in or are secreted from various types of cells. Microvesicles secreted from cells include: (i) exosomes, vesicles having a diameter of 30 to 100 nm that originate from cells; (ii) ectosomes (also called shedding microvesicles (SMVs)), vesicles that are released directly from plasma membranes and have a diameter of 50 to 1000 nm; and (iii) apoptotic blebs, vesicles secreted from dying cells that have a diameter of 50 to 5000 nm.

Using an electron microscope, it has been confirmed that exosomes are not directly released from a plasma membrane, but rather originate from specific intracellular regions called multivesicular bodies (MVBs), with fuse with the plasma membrane and are then released into the extracellular environment as exosomes. Exosomes are secreted from various different cell types under both normal and pathologic states. Red blood cells, various kinds of immune cells (such as B-lymphocytes, T-lymphocytes, dendritic cells, blood platelets, and macrophages), and tumor cells produce and secrete exosomes.

Microvesicles may contain microRNAs (miRNAs), which may be used to identify the status of cells or organisms. The status may be a disease, for example, cancer, hereditary diseases, heart diseases, or neuronal diseases, such as schizophrenia.

Existing methods of isolating microvesicles are performed by combining microvesicles and antibodies to immuno-capture microvesicles. Such methods may cause a bias due to masking of antibody recognition sites by conformational changes of a protein, microvesicle heterogeneity, protein interactions, etc. Furthermore, many existing methods require a complicated process, a high-cost apparatus, or a large sample volume.

Therefore, there is a need for improved methods of efficiently isolating microvesicles from a small amount of sample.

SUMMARY

Provided are compositions to isolate a vesicle.
Provided are kits to isolate a vesicle.
Provided are methods of isolating a vesicle.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
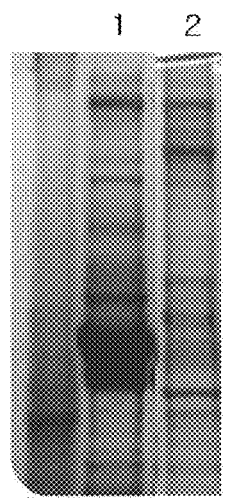
FIG. 1A is an electrophoresis gel image illustrating affinity between human serum and a protein G bead or a bead with sulfobetaine moieties, respectively (wherein 1; a protein G bead, 2; a bead with sulfobetaine moieties).

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an aspect of the present invention, a composition to isolate a vesicle comprises a compound having zwitterion moieties.

A zwitterion, as known as an amphoteric ion or an ampholite ion, refers to an ion which has both a positive electrical charge and a negative electrical charge. Because the positive and negative electrical charges are balanced, a zwitterion has a net charge of zero as a whole molecule, but has a large dipole moment. For example, a zwitterion may have the formula below.

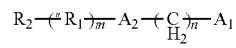

In the formula, $A_1$ and $A_2$ may have a positive or a negative electrical charge, respectively, and $A_1$ and $A_2$ may be functional groups having electrical charges that are opposite to each other. $A_1$ may be a functional group having a positive electrical charge while $A_2$ may be a functional group having a negative electrical charge, or vice versa. Examples of a functional group having a positive electrical charge are an ammonium, a sulfonium, or a phosphonium. Examples of a functional group having a negative electrical charge are carboxylic acid, phosphoric acid, or phosphonic acid.

In the formula, $R_1$ may be an aliphatic hydrocarbon or a cyclic hydrocarbon. An aliphatic hydrocarbon is a compound composed of only carbon atoms and hydrogen atoms wherein the carbon atoms are joined together in chains. For example, an aliphatic hydrocarbon may be a $C_{1-8}$ alkane, a $C_{1-8}$ alkene, or a $C_{1-8}$ alkyne. In addition, an aliphatic hydrocarbon may be a polyacrylate which is a polymer of an acrylic acid. For example, a cyclic hydrocarbon may be an aromatic hydrocarbon. An aromatic hydrocarbon is a hydrocarbon-based compound including a benzene ring and a derivative thereof from the cyclic hydrocarbons. For example, an aromatic hydrocarbon may be a $C_{6-10}$ aromatic hydrocarbon.

In the formula, $R_2$ may be an amine, a carboxyl group, or a hydroxyl group.

In the formula, n may be from about 1 to about 100. For example, n may be from about 1 to about 80, from about 1 to about 60, from about 1 to about 40, from about 1 to about 20, from about 1 to about 10, or from about 1 to about 5.

In the formula, m may be from about 1 to about 100. For example, m may be from about 1 to about 80, from about 1 to about 60, from about 1 to about 40, from about 1 to about 20, from about 1 to about 10, or from about 1 to about 5.

A zwitterion moiety may be, for example, sulfobetaine (SB), carboxybetaine, phosphorylcholine, or a combination thereof.

A zwitterion moiety may be 3-((3-aminopropyl)dimethylammonio)propane-1-sulfonate (sulfobetaine), dimethyl-(2-hydroxyethyl)-(3-sulfopropyl)ammonium (sulfobetaine), 4-aminophenylphosphorylcholine (phosphorylcholine), carboxybetaine methacrylate (carboxybetaine), carboxybetaine methacarylamine (carboxybetaine), or a salt form thereof, for example, pyridinium, sodium, potassium, quaternary ammonium, acetate, chloride, citrate, cyanide, nitrate, or nitrite.

A compound comprising zwitterion moieties may be a compound conjugated with zwitterion moieties and a polymer. The polymer may be any polymer known to one of ordinary skill in the art. Examples of the polymer may be polyethylene, polypropylene, polyacrylate, polyurethane, polystyrene, or a combination thereof. Zwitterion moieties and a polymer may be conjugated by any method known to one of ordinary skill in the art. For example, zwitterions moieties and a polymer may be conjugated by a cross linking of 1-ethyl-3-(3-dimethylaminopropyl)carbodiimide/N-hydroxysuccinimide (EDC/NHS).

A compound comprising zwitterion moieties may be fixed on a solid support. The solid support may be any solid support known to one of ordinary skill in the art. The solid support may be, for example, a magnetic metallic bead such as a $Fe_2O_3$ magnetic bead, a gold bead, or a silver bead, a silica bead, a polystyrene plate, a polymer bead such as a polystyrene bead or a polycarbonate bead, a glass bead, a cellulose bead, a melamine bead, an inorganic bead, or a combination thereof.

A vesicle refers to a membranous structure that is surrounded by a lipid bilayer. For example, the vesicle may be a liposome or a microvesicle. A microvesicle means a small vesicle having a membranous structure that originates from cells. The term "microvesicles" may be interchangeably used with the terms "circulating microvesicles" or "microparticles". Microvesicles may exist inside cells or may be secreted from cells. Microvesicles secreted from cells may include exosomes, ectosomes (shedding microvesicles (SMVs)), apoptotic blebs, or any combination thereof. The exosomes may be membranous vesicles of about 30 to about 100 nm in diameter that originate from cells. The ectosomes (SMVs) may be large membranous vesicles of about 50 to about 1000 nm in diameter that are released directly from plasma membranes. The apoptotic blebs may be vesicles of about 50 to about 5000 nm in diameter that are secreted from dying cells. In vivo microvesicles may contain microRNAs (miRNAs) or messenger RNAs (mRNAs). Surface proteins of the microvesicles may be disease-specific markers.

According to another aspect of the present invention, a kit to isolate a vesicle includes a compound comprising zwitterion moieties.

According to another aspect of the present invention, a method of isolating a vesicle from a sample includes incubating a compound comprising zwitterion moieties with the sample comprising a vesicle to bind the compound to the vesicle in a reaction mixture; and isolating the vesicle from the reaction mixture.

The method includes incubating a compound comprising zwitterion moieties with the sample comprising a vesicle to bind the compound to the vesicle.

A sample may be a body fluid sample or cell culture sample. Examples of the body fluid are urine, mucus, saliva, tears, blood plasma, serum, sputum, spinal fluid, hydrothorax, nipple aspirate, lymph fluid, airway fluid, intestinal fluid, genitourinary fluid, breast milk, fluid in lymphatic system, semen, cerebrospinal fluid, fluid in organ system, ascites, cystic neoplasm fluid, amniotic fluid, or a combination thereof.

A cell or a cell residue may be removed from a sample. The cell may be a living cell or a dead cell. A cell or a cell residue may be removed by any method known to one of ordinary skill in the art. For example, a sample may be pretreated by a separation using a solid support, a centrifugal force, a density gradient centrifugation, an ultracentrifugation, a filtration, a dialysis, an immune-affinity column using antibodies, a free-flow electrophoresis, or a combination thereof.

Incubation may be performed in vitro. For example, incubation may be performed at room temperature and may be carried out while mixing the reactants.

The method of isolating a vesicle from a sample further includes isolating the vesicle from the reaction mixture.

The isolating of the vesicle from the reaction mixture may be performed by, for example, a removal or a washing of the reaction mixture, or a combination thereof. The isolating of the vesicles from the reaction mixture may be performed by binding the vesicle to a compound comprising zwitterions moieties fixed on a solid support.

The isolating method described above may further include a method of detecting the isolated vesicle. The detecting of the isolated vesicle may use any method known to one of ordinary skill in the art. For example, the isolated vesicle may be detected by staining a vesicle, observing using an electron microscope, or using a ligand that is conjugated with a fluorescent substance. When the fluorescent substance is fluorescent protein, the intensity of the fluorescent light caused by ultraviolet irradiation may be detected by using a fluorophotometer.

The detecting method described above may further include a method of isolating a nucleic acid by lysing the isolated vesicle; and analyzing the nucleic acid of the vesicle by amplifying the isolated nucleic acid. Lysis of the vesicle may be performed in the presence of a solvent including, for example, a chaotropic salt, an organic solvent, or a surfactant. Lysis of the vesicle may be performed by, for example, heating, stirring, rotating, vortexing, or a combination thereof. A nucleic acid is a polymer material composed of a purine base or a pyrimidine base, glucose, and a phosphoric acid. A nucleic acid may be, for example, mRNA or microRNA (miRNA). For example, a nucleic acid may be amplified by a reverse-transcription polymerase chain reaction. By analyzing the amplified nucleic acid, the nucleic acid of the vesicle may be analyzed.

The composition, the kit, and the method of isolating a vesicle in a sample including a compound that has zwitterion moieties may suppress nonspecific adsorption of proteins within a biological sample and improve selective isolation of a vesicle and efficiency of the isolation. In addition, the composition, the kit, and the method may be used to analyze vesicles, and proteins, glycoprotein, lipids, or nucleic acids thereof.

Example 1

Preparation of Beads Including Sulfobetaine Moieties 1-1. Couplings for Polymers Including Carboxylic Acids on Surfaces of Magnetic Beads 100 µl of Dynabeads® M-270 Amine (Invitrogen™) were washed twice by 200 µl of a buffer solution which is 0.1 M 2-(N-morpholino)ethanesulfonic acid (MES), 0.5 M NaCl, and pH 6.0, and then re-suspended in 100 µl of the buffer solution. 48 µl of a solution that diluted 35% w/v of polyacrylate (Aldrich) to 1/10 was mixed with 340 µl of the buffer solution, to then be added to and mixed well with beads. 54 µl of 75 mg/ml ethyl-3-dimethyl-aminopropyl carbodiimide (EDC) solution (in distilled water) and 54 µl of 75 mg/ml N-hydroxysuccinimide (NHS) solution (in distilled water) were added to the beads to then be rotated for 1 hour. Next, the beads were washed twice by 400 µl of the buffer solution, and were re-suspended by 400 µl of the buffer solution.

1-2. Surface Treatments using Zwitterion Moieties on Surfaces of Magnetic Beads

The prepared beads according to the method of Example 1-1 were washed twice by 400 µl of a buffer solution which is 0.025 M MES and has a pH of 6.0.

54 µl of 75 mg/ml EDC solution (in 0.025 M MES and pH 6.0), 54 µl of 75 mg/ml NHS solution (in 0.025 M MES and pH 6.0), and 380 µl of the buffer solution were all added and mixed well, and then rotated for 30 minutes. The beads were again washed twice by 400 µl of the buffer solution, and were re-suspended by 400 µl of the buffer solution. Then, zwitterions moieties of 100 µg/µl (of distilled water) were added and rotated for 2 hours and washed twice with 400 µl of the buffer solution.

1-3. Analysis of Synthesized Beads

The amount of sulfur atoms contained in the synthesized beads was confirmed using a time of flight secondary ion mass spectrometry (ToF-SIMS) (Nano TOF TRIFT V, UlvacPHI, Kanagawa, Japan). Also, the quantity of surface electric charges of the synthesized beads was measured by using a zeta potential analyzer (Malvern Instruments, Malvern, U.K.).

Example 2

Measurements of Affinities of Human Serum and Beads Including Sulfobetaine Moieties 300 µl of human serum (clinical sample) was added to 30 µl of beads prepared according to Example 1-2, and then rotated for 4 hours. After removing the supernatant, precipitates were washed 1 time by 300 µl of 1×PBS, and then rotated for additional 3 hours in 300 µl of 1×PBS. After removing the supernatant, precipitates were washed 1 time by 300 µl of 1×PBS. After removing the supernatant, 10 µl of denaturation solution (Invitrogen) was added to the precipitates. Proteins bound to the beads were separated by heating at 100° C. for 10 minutes.

The separated proteins were electrophoresed, and the non-specific adsorption between the beads and the proteins was confirmed by staining the electrophoresis gel with Coomassie Blue (Invitrogen). As shown in FIG. 1A, it was confirmed that the protein G beads (Invitrogen) had very large amount of the non-specific adsorptions while the beads with sulfobetaine moieties had small amount of the non-specific adsorptions.

Figure 1B:
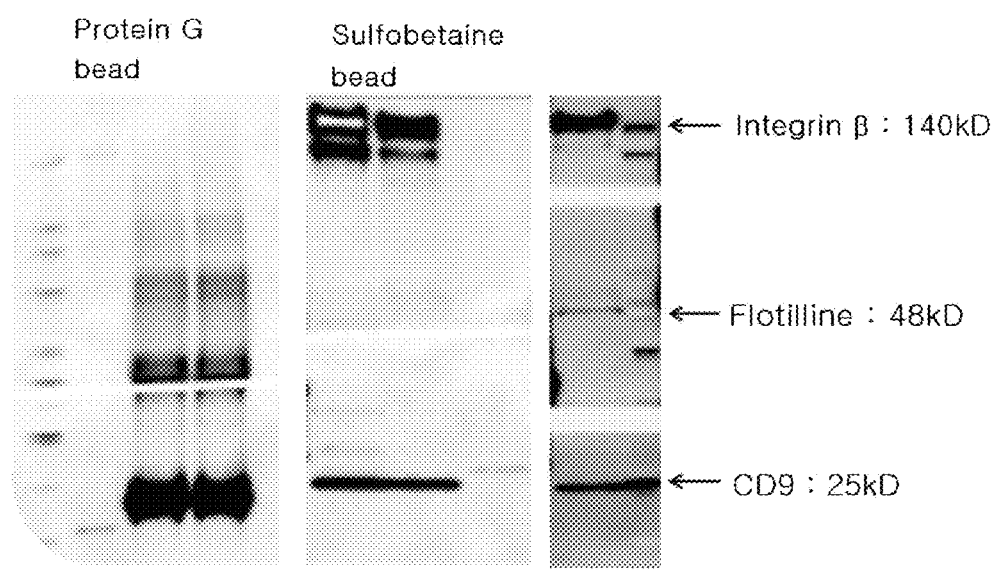
FIG. 1B is an electrophoresis gel image showing a result of Western blotting.

Western blotting was performed with anti-integrin β antibody (Abcam), anti-CD9 antibody (Novus Biological), and anti-flotilline antibody (BD Bioscience) against integrin β, CD9, and flotilline, respectively, that are known exosome markers. As shown in FIG. 1B, in the protein G beads, the exosome marker was not detected at all. However, in the beads with sulfobetaine moieties, integrin β, CD9, and flotilline were detected.

Example 3

Measurement of Affinity Between Beads with Sulfobetaine Moieties and Serum without Microvesicles In order to confirm the result of Example 2, serum without microvesicles and beads with sulfobetaine moieties were bound using ultracentrifugation (110,000 g).

Figure 2:
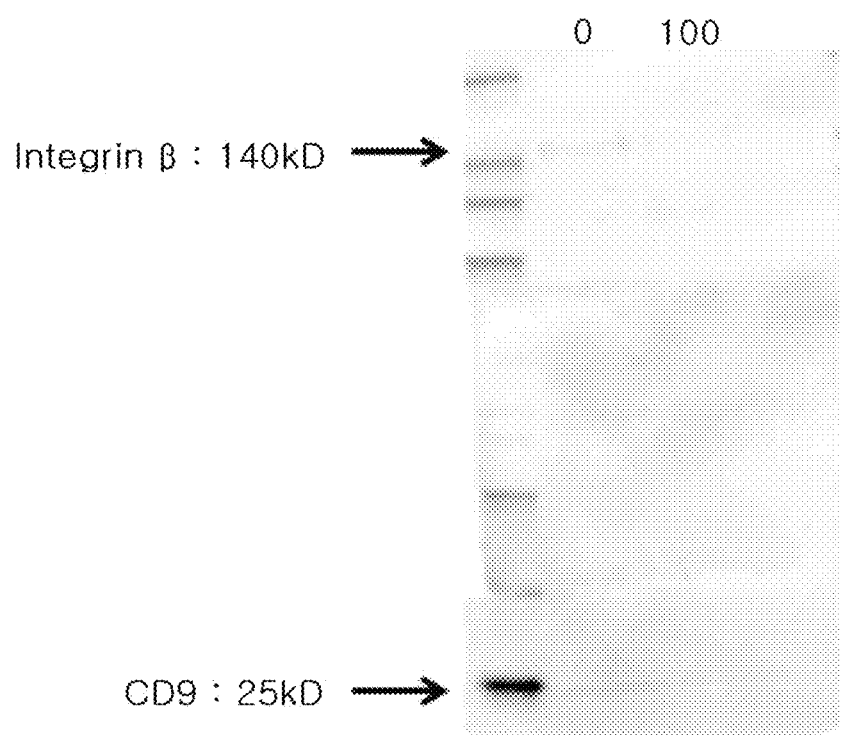
FIG. 2 is an electrophoresis gel image showing a result of Western blotting illustrating affinity between human serum without microvesicles (0=bead without sulfobetaine moieties) and a bead with sulfobetaine moieties (100=bead with sulfobetaine moieties)

As shown in FIG. 2, integrin β and CD9 were not detected when serum without microvesicles and beads with sulfobetaine moieties were bound. Therefore, it was confirmed that integrin β, CD9, and flotilline that were detected in Example 2 originated from microvesicles.

Example 4

Observation of Binding Beads with Sulfobetaine Moieties and Serum without Microvesicles The beads with sulfobetaine moieties prepared according to a method of Example 1 and human serum were bound. Then, microvesicles were directly observed by using scanning electron microscope (SEM) (S-5500, Hitachi, Tokyo, Japan).

Figure 3:
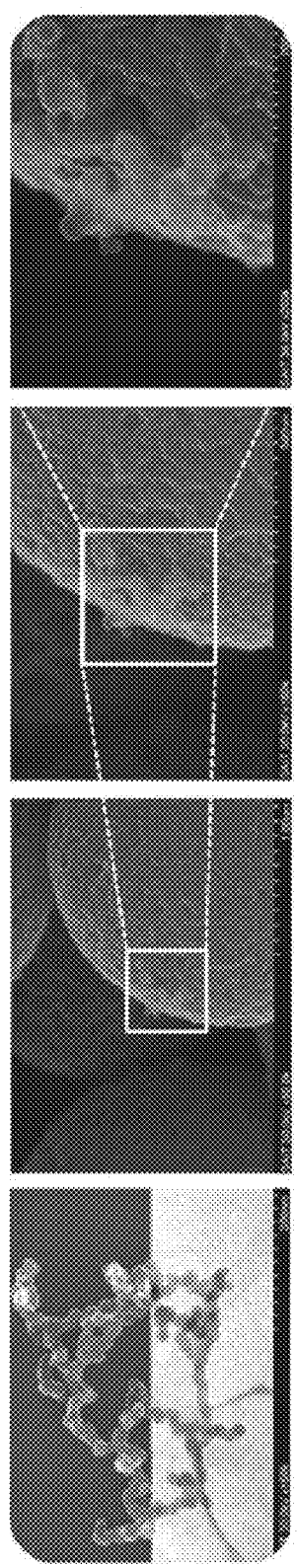
FIG. 3 is a scanning electron microscope (SEM) image showing microvesicles bound to a bead with sulfobetaine moieties.

As shown in FIG. 3, the microvesicles bound on surfaces of the beads with sulfobetaine moieties were observed.

Example 5

Confirmation of Detection Limit of Beads with Sulfobetaine Moieties

Detection limit of the beads with sulfobetaine moieties was confirmed depending on the amount of human serum. 100 µl, 200 µl, and 300 µl of human serum were bound to 100 µl of the beads with sulfobetaine moieties, respectively, for electrophoresis and Western blotting.

Figure 4:
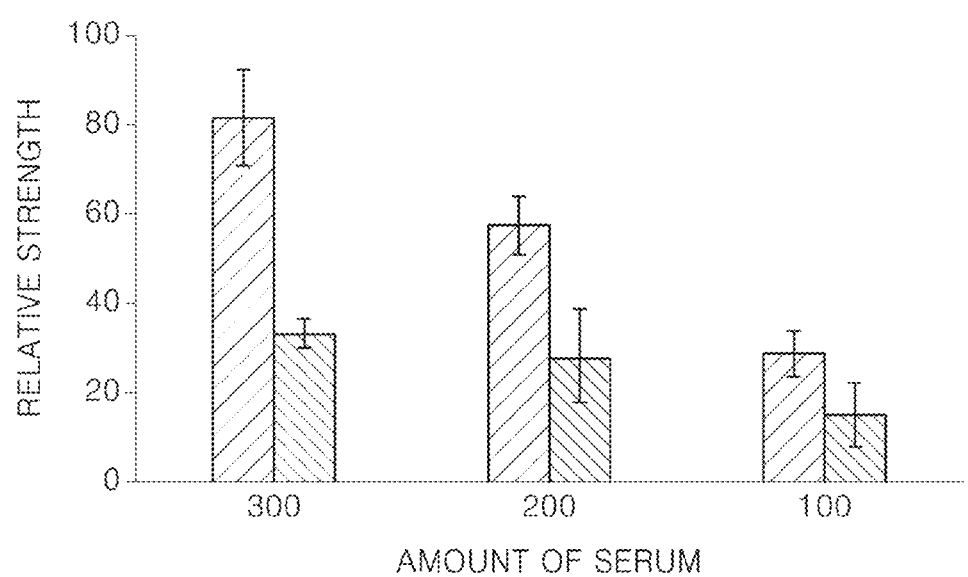
FIG. 4 is a graph showing a detection limit of a bead with sulfobetaine moieties depending on the amount of serum.

As shown in FIG. 4, it was confirmed that as the amount of serum was decreasing, the amounts of integrin β and CD9 were also decreasing in a linear manner (; integrin β, ; CD9). It was also confirmed that microvesicles may be isolated in 100 µl of a very small amount of serum in the presence of the beads with sulfobetaine moieties.

Example 6

Isolation of Microvesicles from Serum of Patients with Benign Tumors and Serum of Patients with Malignant Tumors Microvesicles were isolated from serum of patients with benign tumors or malignant tumors by using the beads with sulfobetaine moieties. Then, integrin β, CD9, and flotilline in serum were detected by electrophoresis and Western blotting. The results are shown in FIG. 5.

Figure 5:
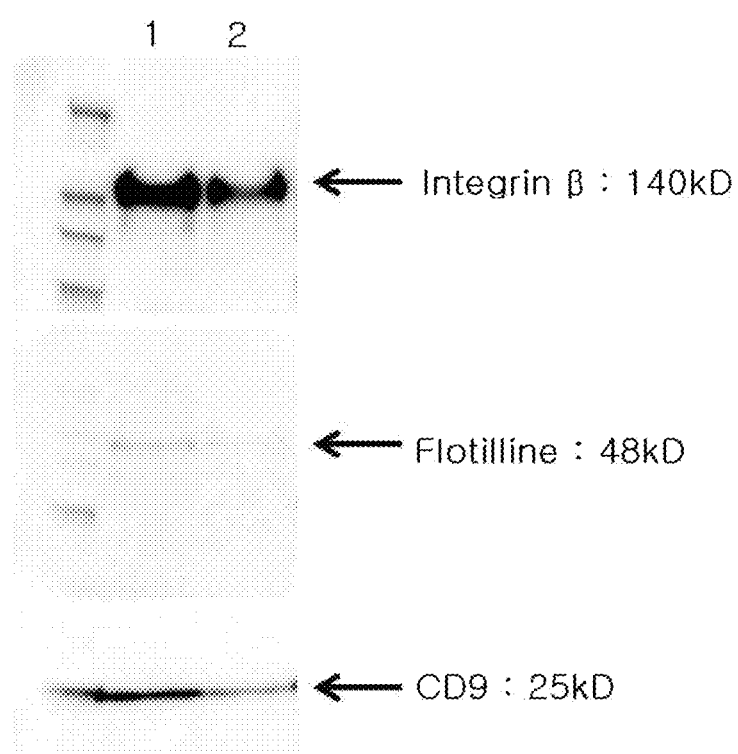
FIG. 5 is an electrophoresis gel image showing microvesicles isolated from serum of patients with benign tumors and malignant tumors, respectively.

As shown in FIG. 5, the possibility of using beads with sulfobetaine moieties to detect exosomes in molecular diagnostics is confirmed.

Example 7

Detection of Nucleic Acids from Microvesicles

Microvesicles were isolated by binding serum of a patient with malignant tumors and the beads with sulfobetaine moieties. In isolated microvesicles, 20 μl of 0.5% Triton X-100 in 1×PBS including 700 mM NaCl was added thereto, to then be incubated for 20 minutes to dissolve microvesicles. Next, miRNA was detected from the lysed microvesicles by using mercury LNA™ Universal RT microRNA PCR kit (Exiqon). In particular, a reverse transcription reaction was performed at 42° C. for 1 hour and at 95° C. for 5 minutes, respectively, followed by a polymerase chain reaction (PCR) at 95° C. for 10 seconds and 60° C. for 1 minute, respectively, repeated for 45 cycles.

The results are shown in Table 1.

TABLE 1

| miRNA | Cp value |
|---|---|
| miR-19b | 27.92 |
| miR-20a | 29.19 |
| miR-126 | 27.49 |
| miR-24 | 28.55 |
| miR-223 | 25.47 |

As shown in Table 1, 5 types of miRNAs were detected from the isolated microvesicles.

What is claimed is:

1. A method of isolating a vesicle from a sample, the method comprising:
   incubating a compound comprising zwitterionic moieties with a sample comprising a vesicle to form a reaction mixture wherein the compound binds to the vesicle; and
   isolating the vesicle from the reaction mixture,
   wherein the sample is a body fluid sample or cell culture sample from which a cell or a cell residue has been removed.

2. The method of claim 1, wherein the sample is urine, mucus, saliva, tears, blood plasma, serum, sputum, spinal fluid, hydrothorax, nipple aspirate, lymph fluid, airway fluid, intestinal fluid, genitourinary fluid, breast milk, fluid in lymphatic system, semen, cerebrospinal fluid, fluid in organ system, ascites, cystic neoplasm fluid, amniotic fluid, or a combination thereof.

3. The method of claim 1, wherein the compound comprising zwitterionic moieties is fixed on a solid support.

4. The method of claim 1, further comprising detecting the isolated vesicle.

5. The method of claim 1, wherein the zwitterionic moieties have the following formula:

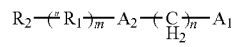

wherein $A_1$ and $A_2$ are functional groups having electrical charges that are opposite to each other;
$R_1$ is an aliphatic hydrocarbon or an aromatic hydrocarbon;
$R_2$ is an amine, a carboxyl group, or a hydroxyl group;
n is from 1 to 100; and
m is from 1 to 100.

6. The method of claim 1, wherein the zwitterionic moieties are sulfobetaine (SB), carboxybetaine, phosphorylcholine, or a combination thereof.

7. The method of claim 1, wherein the compound comprising zwitterionic moieties is a polymer comprising zwitterionic moieties.

8. The method of claim 3, wherein the solid support is a magnetic bead, a silica bead, a polystyrene plate, a polystyrene bead, a glass bead, a cellulose bead, or a combination thereof.

9. The method of claim 1, wherein the vesicle is a liposome or a microvesicle.

10. The method of claim 5, wherein $A_1$ is ammonium, sulfonium, or phosphonium, and $A_2$ is carboxylic acid, phosphoric acid, or phosphonic acid; or $A_1$ is carboxylic acid, phosphoric acid, or phosphonic acid, and $A_2$ is ammonium, sulfonium, or phosphonium.

11. The method of claim 5, wherein $R_1$ is a $C_1$-$C_8$ aliphatic hydrocarbon; $R_2$ is a carboxyl group; n is from about 1 to about 10; and m is from about 1 to about 10.

12. The method of claim 10, wherein $R_1$ is a $C_1$-$C_8$ aliphatic hydrocarbon; $R_2$ is a carboxyl group; n is from about 1 to about 10; and m is from about 1 to about 10.

13. The method of claim 11, wherein $R_1$ is a $C_{1-8}$ alkane.

14. The method of claim 12, wherein $R_1$ is a $C_{1-8}$ alkane, a $C_{1-8}$ alkene, or a $C_{1-8}$ alkyne.

15. The method of claim 1, wherein the vesicle comprises a nucleic acid.

16. The method of claim 1, wherein the vesicle comprises miRNA.

17. The method of claim 15, wherein the method further comprises analyzing the nucleic acid.

* * * * *